United States Patent
Watson

(10) Patent No.: US 8,500,733 B2
(45) Date of Patent: Aug. 6, 2013

(54) ASYMMETRIC DUAL DIRECTIONAL STEERABLE CATHETER SHEATH

(75) Inventor: James R. Watson, Santa Rosa, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 793 days.

(21) Appl. No.: 12/705,228

(22) Filed: Feb. 12, 2010

(65) Prior Publication Data

US 2010/0217261 A1    Aug. 26, 2010

Related U.S. Application Data

(60) Provisional application No. 61/154,244, filed on Feb. 20, 2009.

(51) Int. Cl.
*A61B 18/14* (2006.01)

(52) U.S. Cl.
USPC .......................... 606/41; 604/95.04; 604/525

(58) Field of Classification Search
USPC ............... 606/32, 41, 46; 600/149, 433–435; 604/95.04, 95.01–95.05, 525–532; 607/98–100, 607/115
See application file for complete search history.

(56) References Cited

U.S. PATENT DOCUMENTS

| | | | |
|---|---|---|---|
| 5,273,535 A | 12/1993 | Edwards et al. | |
| 5,358,478 A | 10/1994 | Thompson et al. | |
| 5,575,810 A | 11/1996 | Swanson et al. | |
| 6,198,974 B1 | 3/2001 | Webster, Jr. | |
| 6,579,278 B1 * | 6/2003 | Bencini | 604/528 |
| 6,640,120 B1 | 10/2003 | Swanson et al. | |
| 2002/0082585 A1 * | 6/2002 | Carroll et al. | 604/528 |
| 2002/0161330 A1 * | 10/2002 | Nguyen | 604/95.04 |
| 2003/0114832 A1 | 6/2003 | Kohler et al. | |
| 2003/0195495 A1 | 10/2003 | Ryan et al. | |
| 2004/0181136 A1 * | 9/2004 | McDaniel et al. | 600/374 |
| 2005/0131343 A1 * | 6/2005 | Abrams et al. | 604/95.04 |
| 2005/0256452 A1 * | 11/2005 | DeMarchi et al. | 604/95.04 |
| 2006/0095030 A1 | 5/2006 | Avitall et al. | |
| 2007/0225681 A1 | 9/2007 | House | |
| 2008/0300462 A1 | 12/2008 | Intoccia et al. | |

FOREIGN PATENT DOCUMENTS

| | | |
|---|---|---|
| EP | 2135634 A1 | 12/2009 |
| WO | 9411057 A1 | 5/1994 |
| WO | 9915070 A1 | 4/1999 |
| WO | 2004103434 A2 | 12/2004 |
| WO | 2005094661 A1 | 10/2005 |

* cited by examiner

*Primary Examiner* — Michael Peffley
*Assistant Examiner* — Thomas Giuliani
(74) *Attorney, Agent, or Firm* — Seager, Tufte & Wickhem, LLC

(57) ABSTRACT

A steerable catheter sheath for use in directing a catheter into a desired position is provided. The sheath includes an elongated member configured to receive the catheter therein. The distal end of the elongated member is steerable in two directions, each direction having a different bent configuration, e.g., a sharp curve in one direction and an open arching curve in the other direction. A resilient structure having different bending properties in each of its lateral sides is carried in the distal portion of the elongated member and causes the asymmetric bending. In one embodiment, the resilient structure includes a hypotube with a plurality of notches and slits in the sides. In another embodiment, the resilient structure is covered in an outer coating having different durometer portions. The sheath is particularly useful for accessing left and right pulmonary veins when a transseptal entry approach is used into the left atrium.

12 Claims, 16 Drawing Sheets

ASYMMETRIC DUAL DIRECTIONAL STEERABLE CATHETER SHEATH

RELATED APPLICATION DATA

The present application claims the benefit under 35 U.S.C. §119 to U.S. provisional patent application Ser. No. 61/154,244, filed Feb. 20, 2009. The foregoing application is hereby incorporated by reference into the present application in its entirety.

FIELD OF THE INVENTION

The disclosed inventions generally relate to systems and methods for introducing a medical probe adjacent to target tissue, and more particularly to a steerable sheath for intravascularly introducing and positioning a catheter into a body cavity, such as a heart chamber.

BACKGROUND OF THE INVENTION

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract in an organized manner to transport blood from the atria to the ventricles, and to provide timed stimulation of the ventricles. The AV node regulates the propagation delay to the atrioventricular bundle (or "HIS" bundle). This coordination of the electrical activity of the heart causes atrial systole during ventricular diastole. This, in turn, improves the mechanical function of the heart. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria.

Because of a loss of atrioventricular synchrony, people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

One surgical method of treating atrial fibrillation by interrupting pathways for reentry circuits is the so-called "maze procedure," which relies on a prescribed pattern of incisions to anatomically create a convoluted path, or maze, for electrical propagation within the left and right atria. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, not only is the maze procedure technically difficult to do, it also requires open heart surgery and is very expensive.

Maze-like procedures have also been developed utilizing electrophysiology procedures, which involve forming lesions on the endocardium (the lesions being 1 to 15 cm in length and of varying shape) using an ablation catheter to effectively create a maze for electrical conduction in a predetermined path. The formation of these lesions by soft tissue coagulation (also referred to as "ablation") can provide the same therapeutic benefits that the complex incision patterns of the surgical maze procedure presently provides, but without invasive open heart surgery.

Frequently, an arrhythmia aberration resides at the base, or within one or more pulmonary veins, wherein the atrial tissue extends. To treat such an aberration, physicians use one or more catheters to gain access into interior regions of the pulmonary vein tissue for mapping and ablating targeted tissue areas. Placement of mapping and ablation catheters, or alternatively a combined mapping/ablation catheter, within the vasculature of the patient is typically facilitated with the aid of an introducer guide sheath and/or guide wire.

The introducer guide sheath may be introduced into the left atrium of the heart using a conventional retrograde approach, i.e., through the respective aortic and mitral valves of the heart. Alternatively, a more simple approach is to introduce the introducer guide sheath into the left atrium using a transseptal approach, i.e., through the atrial septum (i.e., fossi ovalis). A detailed description of methods for introducing an introducer guide sheath into the left atrium via a transseptal approach is disclosed in U.S. Pat. No. 5,575,810, issued to Swanson et al., which is fully and expressly incorporated herein by reference. Once the guide sheath is inside the left atrium, the catheter must be advanced through the guide sheath, into the left atrium, and then maneuvered into or adjacent to a desired pulmonary vein (typically with the aid of a guidewire) before mapping and/or ablating. The pulmonary vein may be one of the two left pulmonary veins or one of the two right pulmonary veins.

Positioning of the sheath and guidewire are critical to the success of this procedure, since they are the conduit for the ablation catheter and/or mapping catheter. However, the anatomical location of the atrial septum is closer in proximity to the right pulmonary veins than it is to the left pulmonary veins. Thus, once the guide sheath passes through the atrial septum, the right pulmonary veins are substantially immediately adjacent to the distal end of the guide sheath while the left pulmonary veins are located on substantially the opposite side of the left atrium from the distal end of the guide sheath. As a result, the guide sheath must be maneuvered differently when placing the catheter in contact with the left pulmonary veins as opposed to the right pulmonary veins. While steerable guide sheaths can be used to facilitate the introduction of the catheter within the desired pulmonary vein, the simple curves provided by such steerable guide sheaths do not easily allow the guidance of the catheter within both the left and right pulmonary veins.

SUMMARY OF THE DISCLOSED INVENTIONS

In accordance with a first aspect of the disclosed inventions, a steerable catheter sheath is provided. The sheath comprises an elongated member with a distal end, a proximal end and a lumen extending between the proximal end and the distal end, wherein the lumen is configured for receiving a catheter therein. In one embodiment, the sheath also has a handle coupled to the proximal end of the elongated member and a steering mechanism mounted to the handle. In order to steer the sheath in two directions, the sheath includes first and second steering wires that extend through the elongated member. The distal end of the first steering wire is coupled to a first lateral side of the elongated member, wherein tensioning the first steering wire bends the distal end of the elongated member in a first direction to create a first bending configuration. The distal end of the second steering wire is coupled to a second lateral side of the elongated member, wherein tensioning the second steering wire bends the distal end of the elongated member in a second direction to create a second bending configuration.

If a handle with a steering mechanism is present, the proximal ends of the first and second steering wires are coupled to the steering mechanism, such that operation of the steering mechanism tensions one of the first and second steering wires. A shape of the first bending configuration is different from a shape of the second bending configuration. The first bending configuration has a first radius of curvature, and the second bending configuration has a second radius of curvature, wherein the first and second radii of curvature differ. In one embodiment, the first bending configuration is configured for pointing the distal end of the elongated member towards a right pulmonary vein and the second bending configuration is configured for pointing the distal end of the elongated member towards a left pulmonary vein when the elongated member is introduced into the left atrium through the atrial septum.

In an exemplary embodiment, the elongated member comprises an elongated resilient structure having first and second lateral sides to which the distal ends of the first and second steering wires are respectively affixed. The first and second lateral sides of the resilient structure are opposite to each other and have different bending properties. In a further exemplary embodiment, a fulcrum point of the first lateral side of the resilient structure is distal to a fulcrum point of the second lateral side of the resilient structure. In one embodiment, the resilient structure comprises a tube having a first plurality of notches in a first lateral side of the tube and a second plurality of notches in a second lateral side of the tube. The first plurality of notches are configured for bending the distal end of the elongated member into the first bending configuration and the second plurality of notches are configured for bending the distal end of the elongated member into the second bending configuration. The tube further comprises a plurality of slits in a portion of the first lateral side of the tube for allowing the portion of the tube to bend when the elongated member is steered into the second bending configuration and preventing the portion of the tube from bending when the elongated member is steered into the first bending configuration. A fulcrum point of the first lateral side of the tube is located between the slits and the notches on the first lateral side of the tube. Additionally, the fulcrum point of the first lateral side of the tube is distal to a fulcrum point of the second lateral side of the tube.

In another embodiment, the resilient structure comprises a coil and an outer coating, the outer coating having a first portion disposed over a first lateral side of the coil, and a second portion disposed over a second lateral side of the coil, wherein the first and second portions have different durometers. In an exemplary embodiment, the first portion of the coating is disposed over a distal region of the first lateral side of the coil, the second portion of the coating is disposed over the second lateral side of the coil, and a third portion of the coating is disposed over a proximal region of the first lateral side of the coil.

In a further exemplary embodiment, the first, second, and third portions all have different durometers. For example, the first portion has a low durometer, the second portion has a medium durometer, and the third portion has a high durometer.

In another embodiment, a fulcrum point of the first lateral side of the coil is between the distal region and the proximal region of the first lateral side of the coil. Additionally, the fulcrum point of the first lateral side of the coil is distal to a fulcrum point of the second lateral side of the coil.

In one embodiment, a catheter assembly is provided that includes the steerable catheter sheath as described above and a catheter disposed within the lumen of the elongated member. In an exemplary embodiment, the catheter is a tissue ablation catheter.

In accordance with yet another aspect of the disclosed inventions, a method of using the catheter assembly described above is provided. The method includes introducing the elongated member into a left atrium. In one embodiment, the elongated member is introduced into the left atrium using a transseptal approach where the elongated member passes from a right atrium through an atrial septum into the left atrium. The method further comprises tensioning the first steering wire to bend the elongated member in the first direction into the first bending configuration to point the distal end of the elongated member towards a right pulmonary vein. Once the distal end is in a desired position, the ablation catheter is advanced through the lumen of the elongated member such that the ablation catheter distally extends from the elongated member to contact a first target tissue site within or adjacent to the right pulmonary vein. The ablation catheter is then operated to ablate the first target tissue site. After ablation of the first target tissue site, the catheter is retracted into the elongated member.

In an exemplary embodiment, the method further comprises tensioning the second steering wire to bend the elongated member in the second direction into the second bending configuration to point the distal end of the elongated member towards a left pulmonary vein. Once the distal end is in a desired position, the ablation catheter is again advanced through the lumen of the elongated member such that the ablation catheter distally extends from the elongated member to contact a second target tissue site within or adjacent to the left pulmonary vein. The catheter is then operated to ablate the second target tissue site. After the second target tissue site is ablated, the ablation catheter is again retracted into the elongated member.

In one embodiment, the steps of tensioning the first steering wire and tensioning the second steering wire may be performed by operating a steering mechanism on the proximal end of the elongated member. In a further embodiment, tensioning the first steering wire causes compression of a first lateral side of a resilient structure carried by the distal end of the elongated member and tensioning the second steering wire causes compression of a second lateral side of the resilient structure. Still further, in one embodiment, tensioning the first steering wire comprises compressing the first lateral side of the resilient structure and expanding the second lateral side of the resilient structure and tensioning the second steering wire comprises compressing the second lateral side of the resilient structure and expanding the first lateral side of the resilient structure.

In accordance with still another aspect of the disclosed inventions, a method for positioning a catheter is provided. The method includes introducing a catheter guide sheath into an anatomical cavity; introducing the catheter into the guide sheath; deflecting a distal end of the guide sheath in a first direction into a first bending configuration to point the distal end of the guide sheath towards a first target site; operating the catheter to perform a medical procedure at the first target site; deflecting the distal end of the guide sheath in a second direction into a second bending configuration different from the first bending configuration to point the distal end of the guide sheath toward a second target site different from the first target site; and operating the catheter to perform another medical procedure at the second target site.

In an exemplary embodiment, the method also includes advancing the catheter within the guide sheath until a distal end of the catheter extends distally from the distal end of the guide sheath adjacent to the first target site when the distal end of the guide sheath is in the first bending configuration; retracting the catheter within the guide sheath prior to deflecting the distal end of the guide sheath into the second bending configuration; and advancing the catheter within the guide sheath until the distal end of the catheter extends distally from the distal end of the guide sheath adjacent to the second target site when the distal end of the guide sheath is in the second bending configuration.

In one embodiment, the anatomical cavity is a heart chamber, the first target site is a right pulmonary vein, and the second target site is a left pulmonary vein. In a further embodiment, the method includes passing the distal end of the guide sheath from a right atrium to a left atrium through a septal wall. In an exemplary embodiment, the medical procedures are ablation procedures.

In a further exemplary embodiment, the method comprises operating a steering mechanism coupled to a proximal end of the guide sheath to deflect the distal end of the guide sheath into the first bending configuration and the second bending configuration. In a still further exemplary embodiment, deflecting the distal end of the guide sheath in the first direction comprises tensioning a first steering wire, and deflecting the distal end of the guide sheath in the second direction comprises tensioning a second steering wire.

Although the disclosed inventions should not be so limited in their broadest aspects, the use of a steerable catheter sheath in the manner described above allows a user to position the catheter sheath near a target ablation site before the catheter is deployed from the sheath, thereby decreasing the distance traveled by the catheter between the distal end of the sheath and the target tissue site and increasing the ease with which the catheter is retracted back into the sheath after the ablation procedure.

Other features of the disclosed inventions will become apparent from consideration of the following description taken in conjunction with the accompanying drawings.

BRIEF DESCRIPTION OF THE DRAWINGS

The drawings illustrate the design and utility of preferred embodiments of the disclosed inventions, in which similar elements are referred to by common reference numerals, and in which.

DETAILED DESCRIPTION OF THE PREFERRED EMBODIMENTS

Figure 1A:
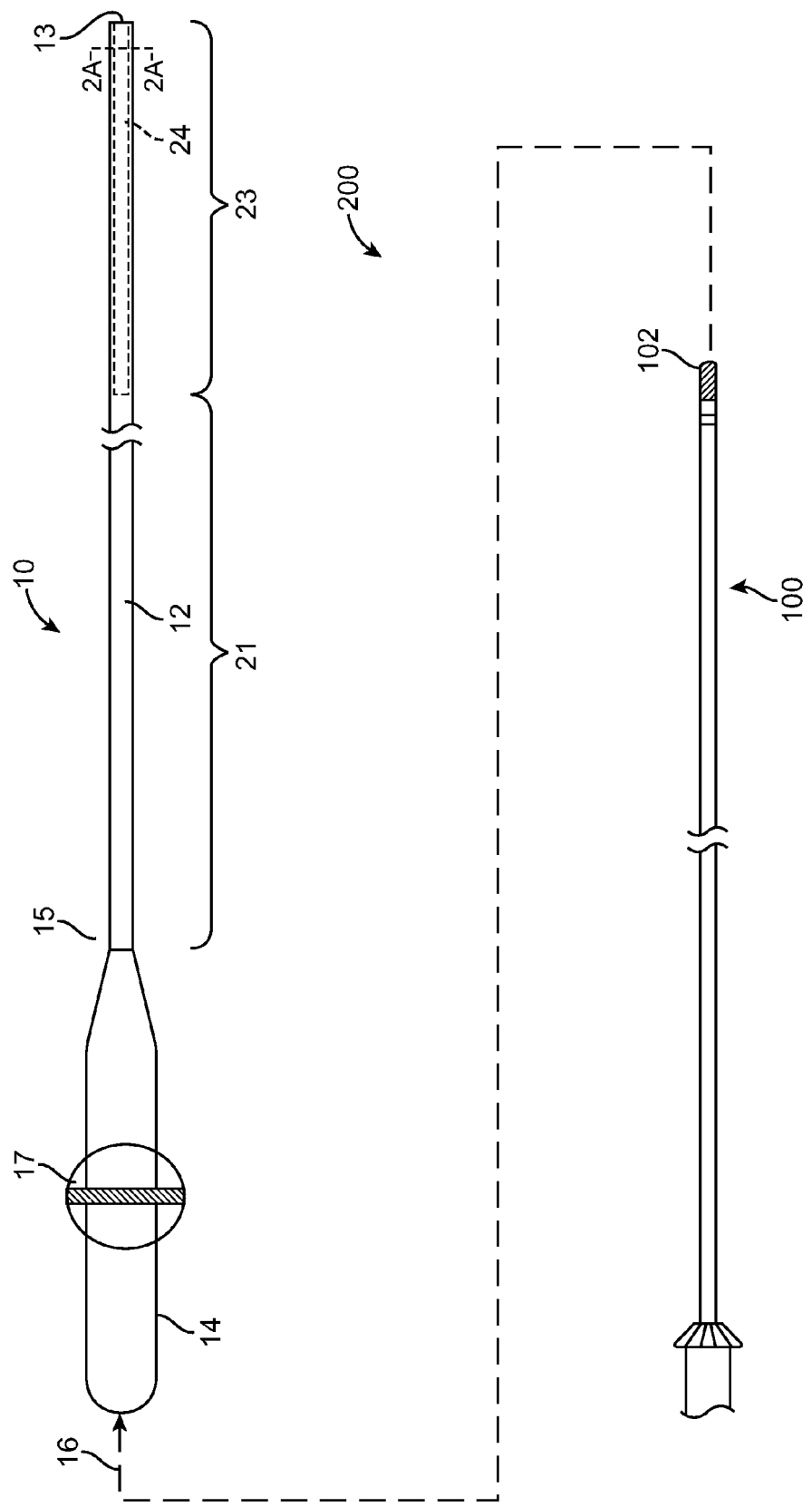
FIG. 1A is a plan view of a catheter assembly including an ablation catheter and a steerable catheter sheath constructed in accordance with the disclosed inventions.
Figure 2A:
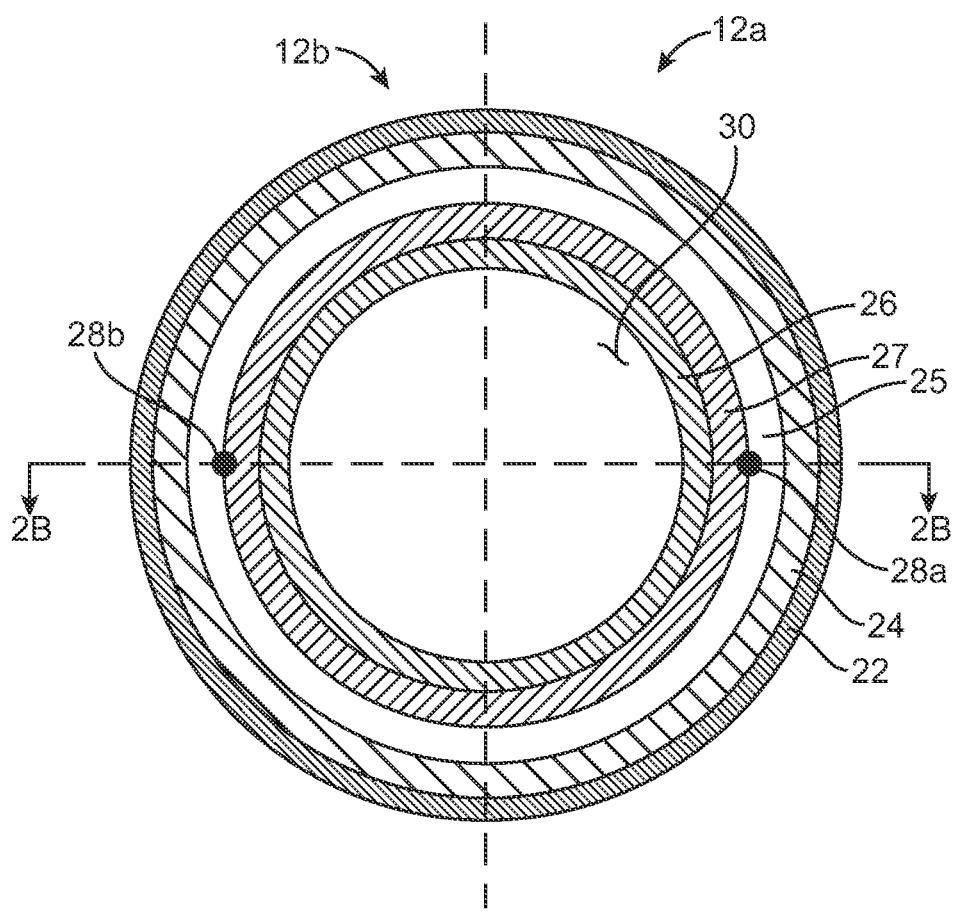
FIG. 2A is a cross-sectional view of the steerable catheter sheath taken along line 2A-2A in FIG. 1A.
Figure 2B:
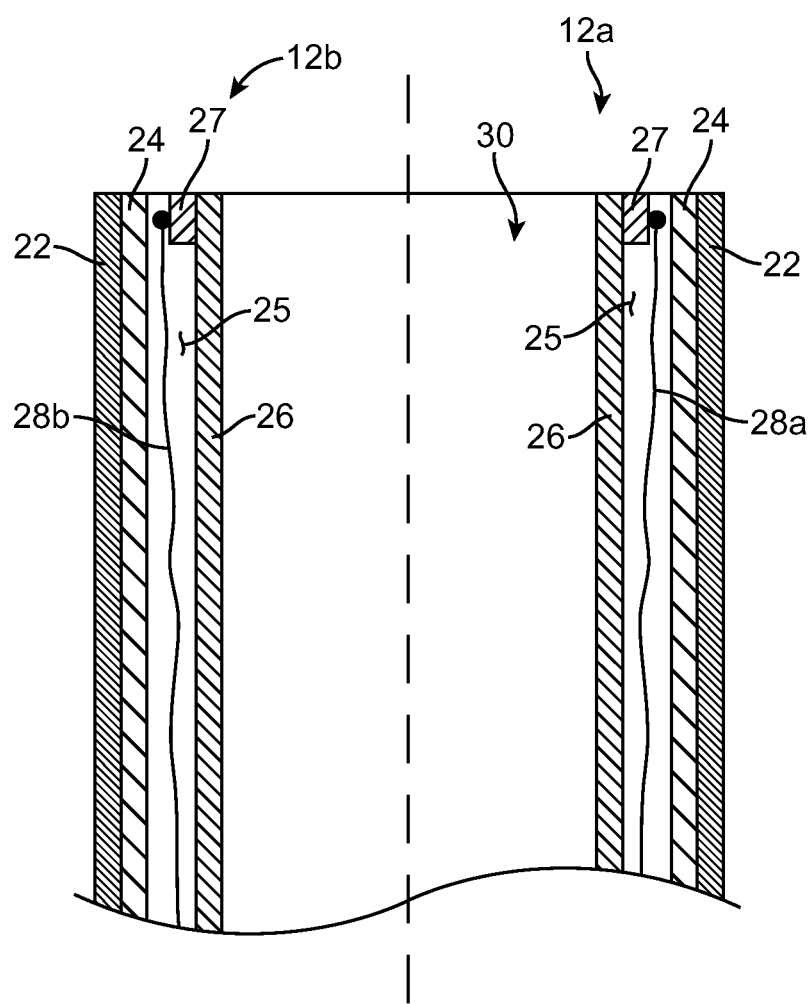
FIG. 2B is a cross-sectional view of the steerable catheter sheath taken along line 2B-2B in FIG. 2A.

Referring to FIGS. 1A, 1A, 2A, and 2B, an exemplary assembly 200 constructed in accordance with the disclosed inventions is shown. The assembly 200 includes a catheter 100 and a steerable catheter sheath 10 sized for receiving the catheter 100 therein. In the illustrated embodiment, the catheter 100 is an ablation catheter or a mapping/ablation catheter and carries ablation and/or mapping elements on a distal end 102 thereof. The assembly 200 may further include a guide wire and/or other therapeutic tools (not shown) to be delivered into the left atrium in a desired position.

Although the steerable catheter sheath 10 is described hereinafter for use in the heart for facilitating introduction of the catheter 100 into desirable positions for mapping and ablating arrhythmia substrates, the sheath 10 may be used within any body lumens, chambers or cavities of a patient for therapeutic and diagnostic purposes in those instances where access to interior bodily regions is obtained through, for example, the vascular system or alimentary canal and without complex invasive surgical procedures. For example, the sheath 10 also has application in the treatment of ailments of the gastrointestinal tract, prostrate, brain, gall bladder, uterus, and other regions of the body.

The sheath 10 generally comprises an elongated body 12, a handle 14 coupled to a proximal end 15 of the elongated body 12, and a lumen 30 extending through the elongated body 12 for allowing the catheter 100, guide wire (not shown), and/or other therapeutic tools (also not shown) to be inserted from a proximal end of the handle 14 towards a distal end 13 of the elongated body 12, as indicated by arrow 16 in FIG. 1A. The elongated body 12 includes a proximal portion 21 and a steerable distal portion 23.

Figure 1B:
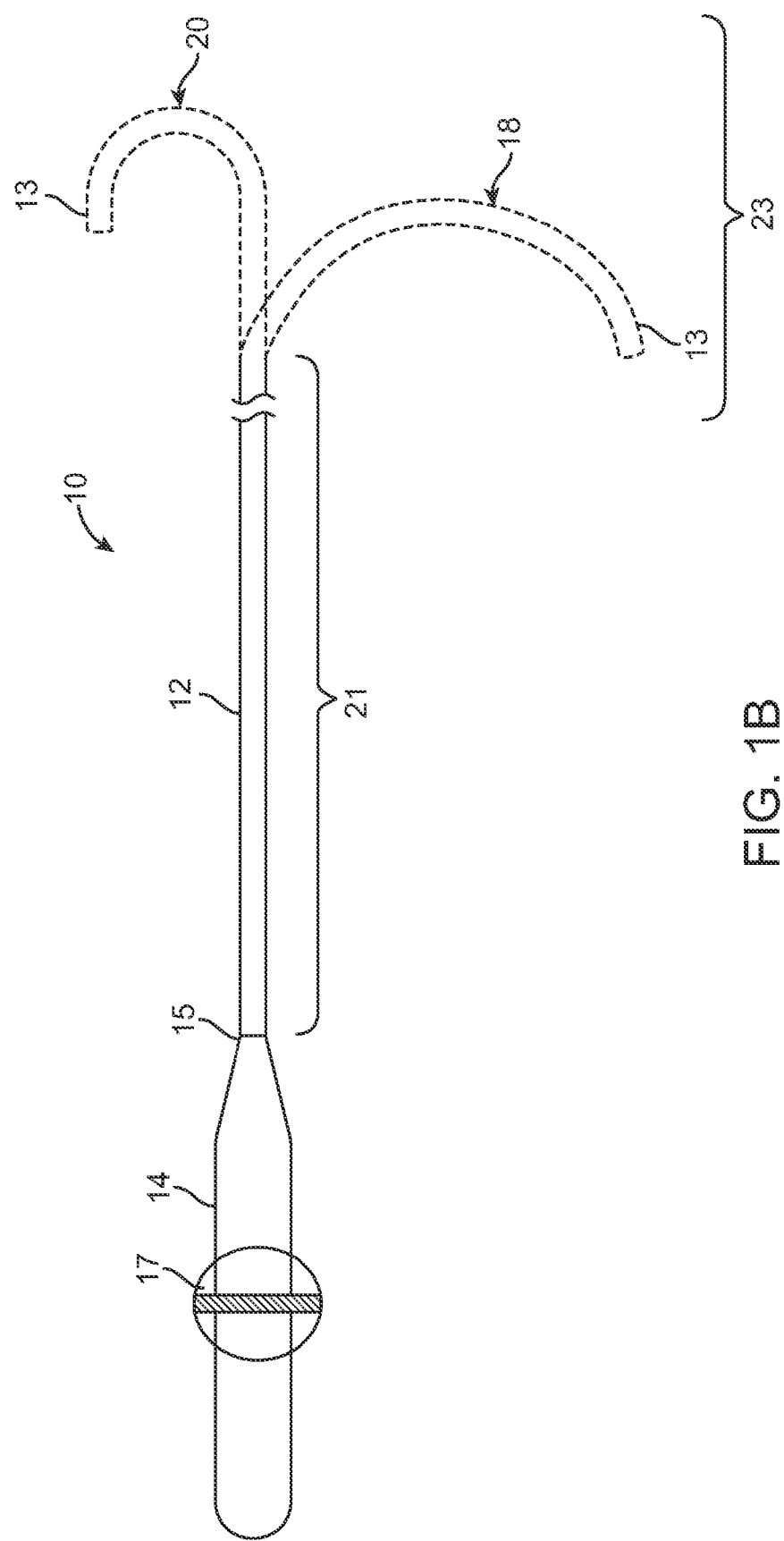
FIG. 1B is a plan view of the steerable catheter sheath constructed in accordance with the disclosed inventions with a first bent configuration and a second bent configuration shown in phantom.

The distal end 13 of the elongated body 12 is configured to be introduced through the vasculature of the patient, and into an anatomical cavity, such as the left atrium of the heart. The distal portion 23 is configured to selectively bend in two directions, each bending direction having its own specific configuration, as shown in phantom in FIG. 1B. The curvature assumed by bending the distal portion 23 to the right is different from the curvature assumed by bending the distal portion 23 to the left. For instance, when deflected to the right, the distal portion 23 assumes a first configuration 18, e.g. a substantially open arch curved profile with a first predetermined circumference. In contrast, when deflected to the left, the distal portion 23 assumes a second configuration 20, e.g. a sharply curved profile with a second predetermined circumference. These different left and right curvatures are referred to herein as asymmetric curves.

In an exemplary embodiment, the second configuration 20 has a substantially smaller radius of curvature than that of the first configuration 18. The specific circumferences, radii of curvature, and shapes that the distal portion 23 will assume is related to parameters such as the size, shape, material of construction, and location of various elements of the elongated body 12. It should be well understood that any desired circumference, radius of curvature, and shape of the two bent configurations may be achieved by adjusting such parameters.

The proximal portion 21 of the elongated body 12 is formed of a composite of Pebax® and stainless steel, or other suitable materials, in the form of a braid, coil, or combination thereof, so that the proximal portion 21 of the elongated body 12 has desired stiffness and torsional properties. The distal portion 23 of the elongated body 12 is formed of a more flexible material so that the distal portion 23 has desired bending properties. The distal portion 23 comprises an elongated resilient structure 24 shown in phantom in FIG. 1A. As best shown in FIGS. 2A and 2B, the distal portion 23 of the elongated body 12 includes a lubricious inner coating 26 disposed on the inner surface of the resilient structure 24 to reduce friction during movement of a catheter or guide wire through the lumen 30, and an outer coating 22 disposed on the outer surface of the resilient structure 24. The resilient structure 24 may be composed of a suitable resilient material, such as stainless steel or nitinol. The inner coating 26 may be PTFE or the like, and the outer coating 22 may be Pebax®, polyethylene, polyurethane, polyolefin, or any other suitable polymeric or bio-compatible material.

The sheath 10 further comprises a steering mechanism 17 incorporated into the handle 14, and a pair of right and left steering wires 28a, 28b extending through the elongated body 12. The steering mechanism 17 is operable to selectively tension the steering wires 28a, 28b, thereby transforming the distal portion 23 of the elongated body 12 from its straight geometry, shown in FIG. 1A, into one of its curved geometries, shown in FIG. 1B.

To this end, the proximal ends of the steering wires 28a, 28b are coupled to the steering mechanism 17 in the handle 14, while the distal ends of the steering wires 28a, 28b are welded or otherwise affixed to a steering ring 27 that is disposed between the inner coating 26 and the resilient structure 24, as shown in FIGS. 2A and 2B. In particular, one of the steering wires (in this case, the right steering wire 28a) is attached to the right lateral side of the steering ring 27 and the other steering wire (in this case, the left steering wire 28b) is attached to the left lateral side of the steering ring 27. The steering wires 28a and 28b may alternatively or additionally be affixed to opposite lateral sides of the resilient structure 24. The steering wires 28a and 28b are free to slide within the space 25 between the resilient structure 24 and the inner liner 26. In an exemplary embodiment, the steering wires 28a and 28b are coated (i.e. with Teflon®, not shown) to reduce friction caused by the steering wires 28a and 28b moving relative to the resilient structure 24 and the inner coating 26. Further details of exemplary steering mechanisms can be found in U.S. Pat. Nos. 6,579,278, 6,198,974, 5,358,478 and 5,273,535, which are expressly incorporated herein by reference.

It should be well understood that, although FIGS. 2A and 2B depict the resilient structure 24 extending over the steering ring 27, the resilient structure 24 may alternatively not extend over the steering ring 27. It should also be well understood that, although the steering wires 28a, 28b and steering ring 27 are depicted as being attached to the distal end 13 of the elongated body 12, the attachment may alternatively be proximal to the distal end 13, depending on the desired bending configurations. In a further alternative, the steering wires 28a and 28b may be attached at different lateral positions along the elongated body 12, in which case the elongated body 12 may include two steering rings wherein the steering wires 28a and 28b are each attached to a different steering ring.

The asymmetric bending of the distal portion 23 of the elongated body 12 results from different bending properties and different fulcrum point positions on the respective lateral sides 12a and 12b of the distal portion 23 of the elongated body 12. There are various ways to achieve the different bending properties and fulcrum point positions. For example, the different bending properties and fulcrum point positions may be incorporated in the resilient structure 24 and/or the outer coating 22 where opposite lateral sides of the resilient structure 24 and/or the outer coating 22 are configured to bend differently when the steering mechanism 17 is operated.

Figure 3A:
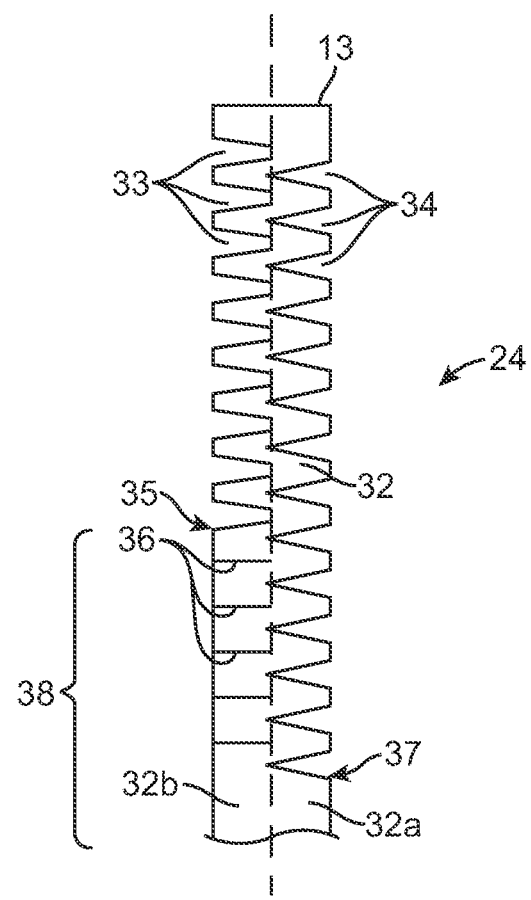
FIG. 3A is a plan view of a first embodiment of a resilient structure.
Figure 3B:
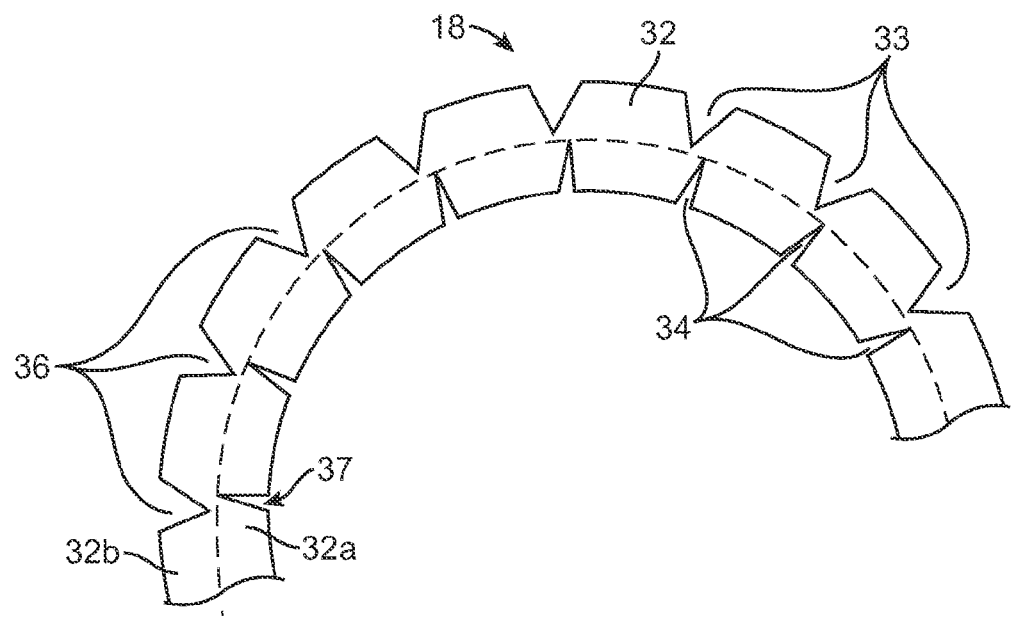
FIGS. 3B and 3C are plan views of the first embodiment of the resilient structure in the first bent configuration and the second bent configuration, respectively.
Figure 3C:
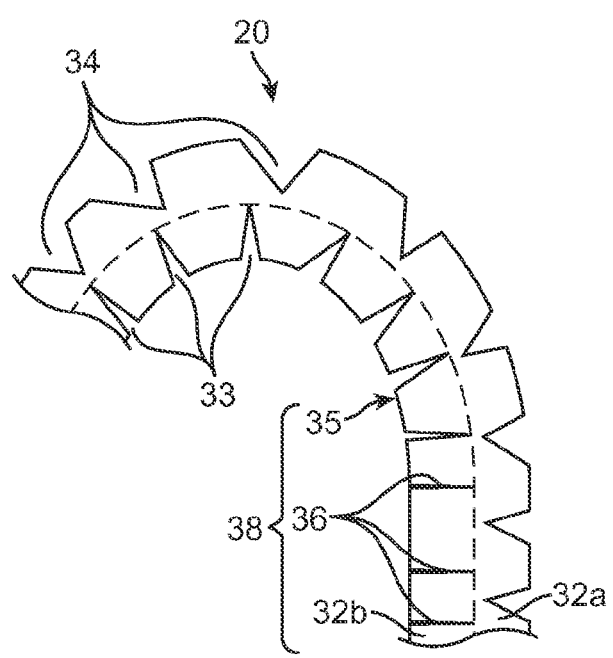

Referring to FIGS. 3A-3C, in an exemplary embodiment, the resilient structure 24 comprises an elongated hypotube 32, a plurality of laser cuts or notches 34 on the right lateral side 32a of the tube 32, and a plurality of laser cuts or notches 33 and a plurality of slits 36 on a left lateral side 32b of the tube 32. The notches 33, 34, and slits 36 are configured in a manner that facilitates the bi-directional asymmetric deflection of the distal portion 23 of the elongated body 12. Specifically, the notches 34 are located between a right side fulcrum point 37 and the distal end 13, the notches 33 are located between a left side fulcrum point 35 and the distal end 13, and the slits 36 are located proximal to the left side fulcrum point 35, but distal to the right side fulcrum point 37. It should be understood that the slits 36 and notches 33 and 34 can be configured to achieve substantially any desired curve circumference, shape, and fulcrum point position, as long as the bi-directional asymmetric deflection of the distal end 13 can be achieved. Thus, the slits 36 and notches 33 and 34 may alternatively have sizes and shapes that are different from those depicted in FIGS. 3A-3C.

The size, shape and spacing of the notches 34 on the right lateral side 32a of the hypotube 32 are configured so that, when the right steering wire 28a (not shown here for clarity; see FIGS. 2A-2B) is tensioned, the distal portion 23 of the elongated body 12 will bend into the first configuration 18 by compressing the notches 34 on the right lateral side 32a, while expanding the notches 33 and slits 36 on the left lateral side 32b, as shown in FIG. 3B. The size, shape and spacing of the notches 33 and the slits 36 on the left lateral side 32b of the hypotube 32 are configured so that, when the left steering wire 28b (not shown here for clarity; see FIGS. 2A-2B) is tensioned, the distal end 13 of the elongated body 12 will bend into the second configuration 20 by compressing the notches 33 on the left lateral side 32b while expanding the notches 34 on the right lateral side 32a, as shown in FIG. 3C. Substantially the entire hypotube 32 is free to bend when steered into the first configuration 18. However, the slits 36 are already completely compressed and do not collapse upon one another, thereby preventing a proximal portion 38 of the hypotube 32 from bending when the hypotube 32 is directed into the second configuration 20.

Figure 4A:
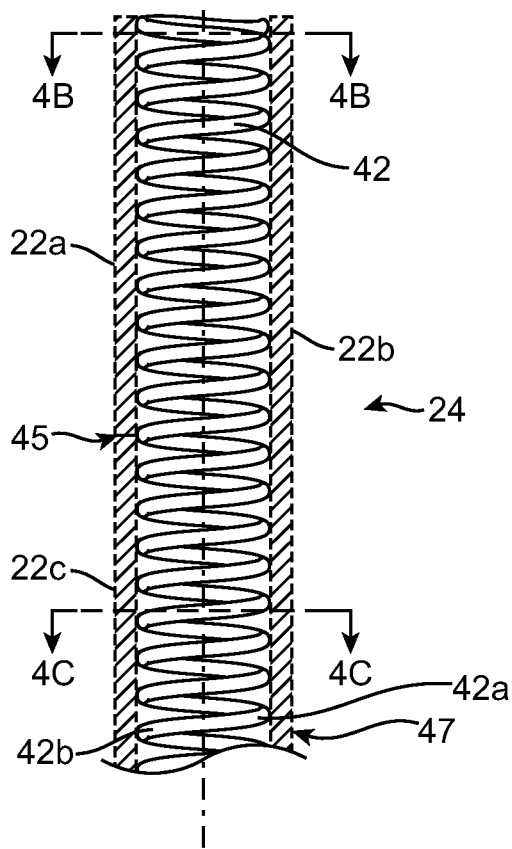
FIG. 4A is a plan view of a second embodiment of a resilient structure and an outer coating shown in phantom.
Figure 4B:
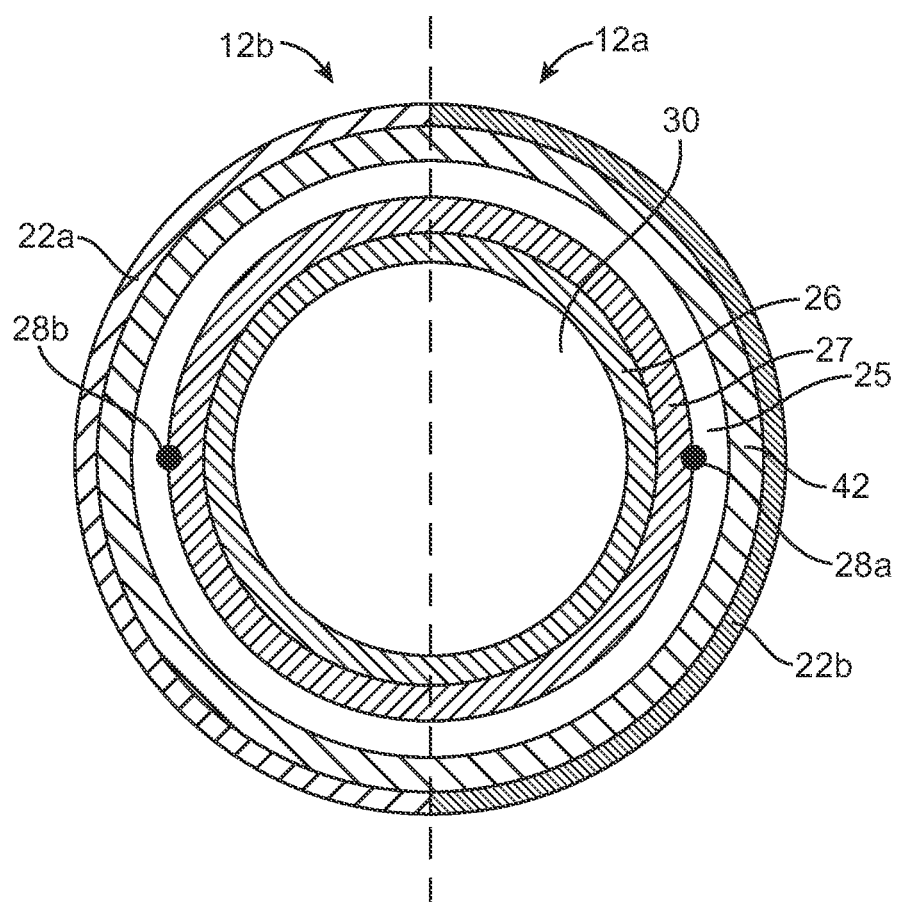
FIGS. 4B and 4C are cross-sectional views of the steerable catheter sheath, according to the second embodiment, taken along lines 4B-4B and 4C-4C, respectively, of FIG. 4A.
Figure 4C:
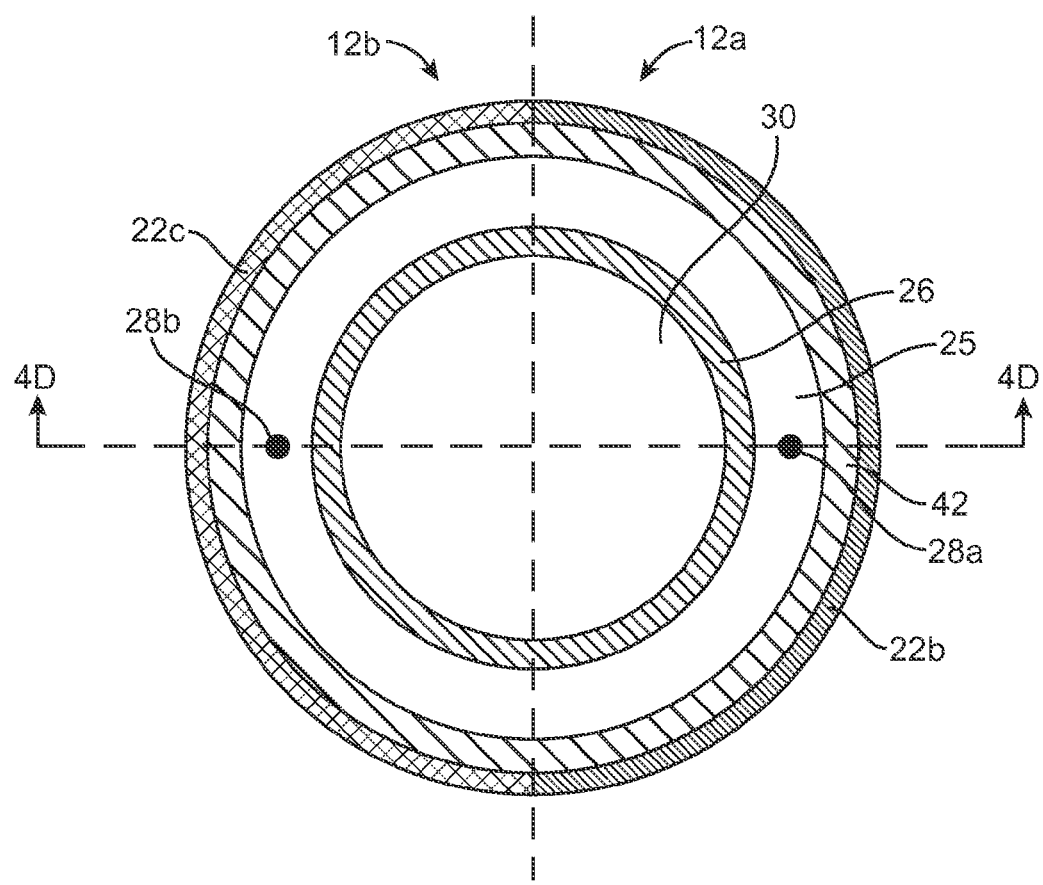
Figure 4D:
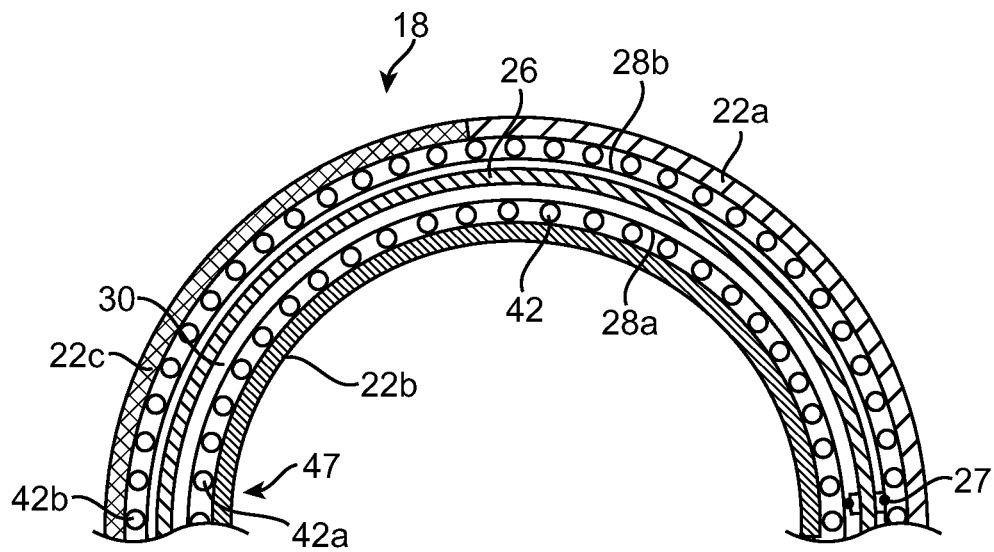
FIGS. 4D and 4E are cross-sectional views of the steerable catheter sheath, taken along line 4D-4D of FIG. 4C, in the first bent configuration and the second bent configuration, respectively.
Figure 4E:
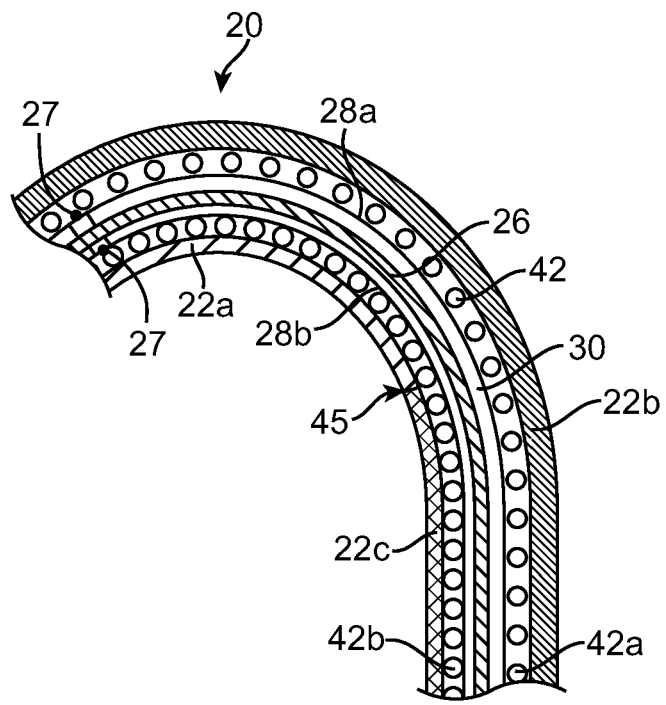
Figure 4F:
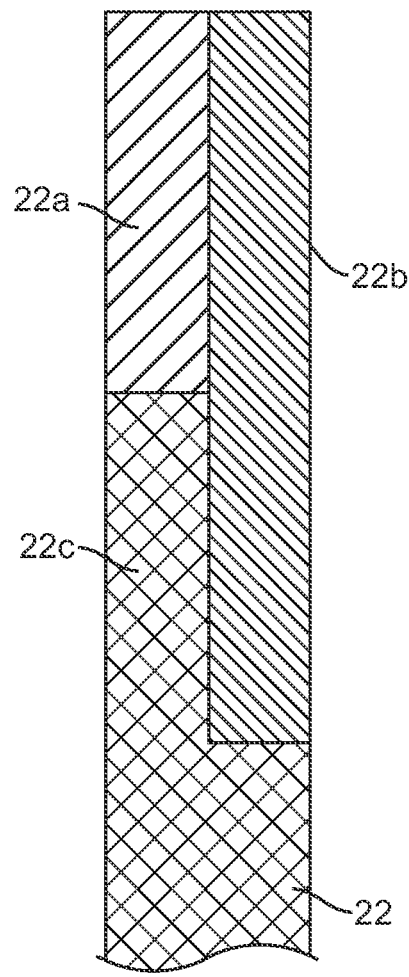
FIG. 4F is a plan view of the distal portion of the steerable catheter sheath with the outer coating constructed in accordance with the second embodiment.

Referring to FIGS. 4A-4F, in another exemplary embodiment, the resilient structure 24 comprises an elongated coil 42 and the outer coating 22 includes portions 22a, 22b and 22c with different durometers. The left lateral side distal portion 22a of the coating has a low durometer, the right lateral side portion 22b of the coating has a medium durometer, and the left lateral side proximal portion 22c has a high durometer. Thus, the stiffness of the outer coating 22 is not uniform, but varies along its length and circumference. The stiffest part of the coating 22 is the left lateral side proximal portion 22c, which is substantially equal in durometer to the coating 22 covering the rest of the elongated body 12 proximal to the resilient structure 24, as best depicted in FIG. 4F.

Each portion 22a, 22b and 22c of the coating extends about halfway around the circumference of the coil 42, as depicted in FIGS. 4B, 4C and 4F. However, it should be well understood that the portions 22a, 22b and 22c may extend around less than half of the circumference of the coil 42 or more than half the circumference of the coil 42. The portions 22a, 22b and 22c of the coating 22 may be formed by co-extrusion, compression melting, flow melting and/or the like. In one embodiment, the coating 22 is applied to the coil 42 by positioning the coil 42 within the coating 22 (which will take the form of a tube) and heat shrinking or the like.

The coating 22 is arranged, such that a fulcrum point 45 is formed between the left lateral side distal portion 22a and the left lateral side proximal portion 22c of the coating, and a fulcrum point 47 is formed just proximal to the right lateral side portion 22b of the coating, with the fulcrum point 45 being distal to the fulcrum point 47. Thus, the durometers and relative locations of the coating portions 22a, 22b and 22c are arranged so that when the right steering wire 28a is tensioned, the distal end 13 of the elongated body 12 will bend into the first configuration 18 by compressing the right lateral side 42a of the coil while expanding the left lateral side 42b of the coil, as shown in FIG. 4D, and when the left steering wire 28b is tensioned, the distal end 13 of the elongated body 12 will bend into the second configuration 20 by compressing the left lateral side 42b of the coil, while expanding the right lateral side 42a of the coil, as shown in FIG. 4E. It should be understood that the coating 22 and the coil 42 can be configured to achieve substantially any desired curve circumference, shape, and fulcrum point position, as long as the bi-directional asymmetric deflection of the distal end 13 can be achieved.

In general, the asymmetric curves provide the user with flexibility in steering the catheter guide sheath 10 into position. The asymmetric curves of the distal portion 23 of the elongated body 12 may be especially advantageous when a transeptal approach is used for entering into the left atrium, i.e., since the first predetermined circumference is larger than the second predetermined circumference, the first configuration 18 is used to point the distal end 13 of the elongated body 12 towards the left pulmonary veins and the second configuration 20 is used to point the distal end 13 of the elongated body 12 towards the right pulmonary veins. Positioning the distal end 13 of the elongated body 12 as close to a target location as possible reduces the distance that an ablation or mapping catheter must distally extend out of the distal end 13 and retraction of the catheter proximally back into the elongated body 12 is simplified.

Figure 5A:
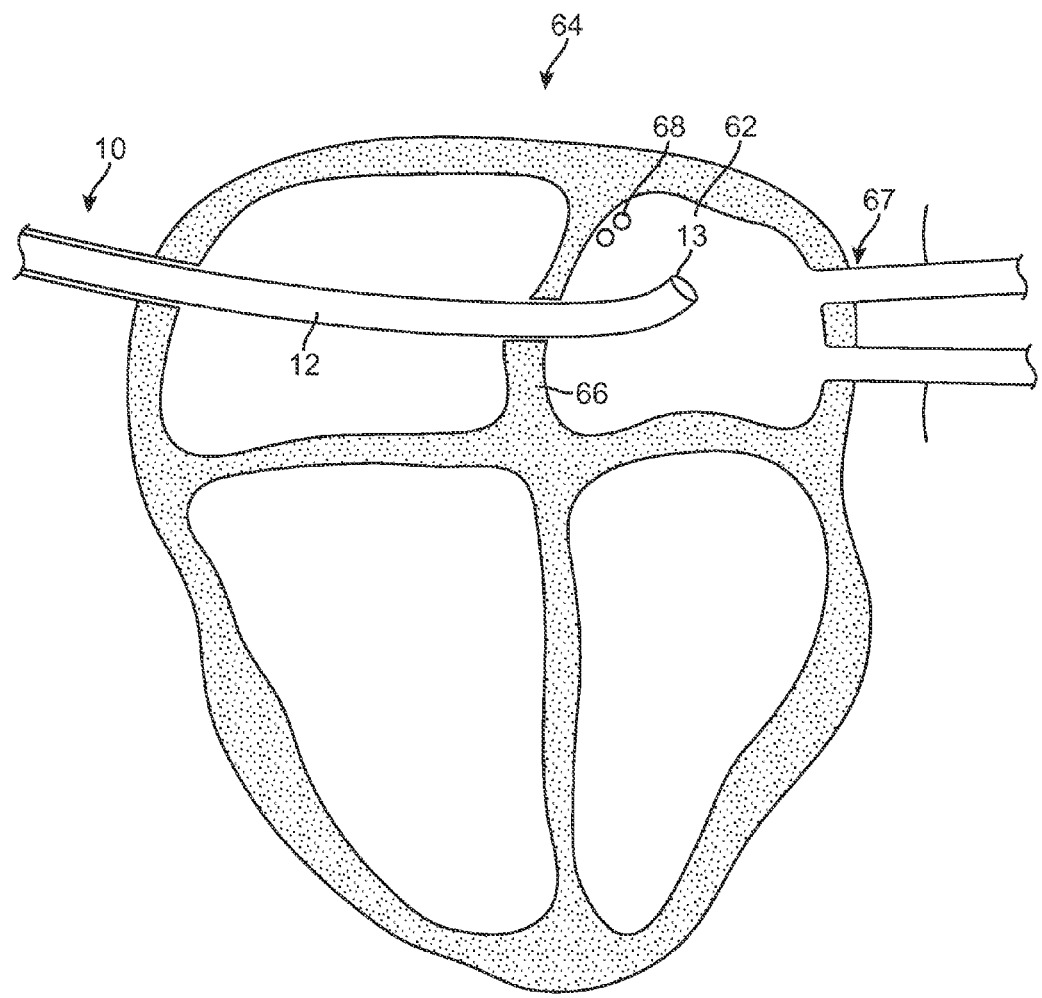
FIGS. 5A-5E are plan views of steps in a method of using the catheter assembly shown in FIG. 1A to direct a catheter into a desired position.

Having described the structure of the catheter guide sheath 10, its operation in positioning the mapping and/or ablation catheter 100 near target tissue in the left and right pulmonary veins within the left atrium of the heart will now be described with reference to FIGS. 5A-5E. It should be noted that other regions within the heart can also be targeted using the steerable catheter guide sheath 10. First, as shown in FIG. 5A, the guide sheath 10 is introduced into the left atrium 62 of the heart 64 using a transeptal approach. A guide catheter or guide wire (not shown) may be used in association with the guide sheath 10 to aid in directing the guide sheath 10 through the appropriate artery toward the heart 64 (i.e., through the inferior vena cava or superior vena cava into the right atrium).

Figure 5B:
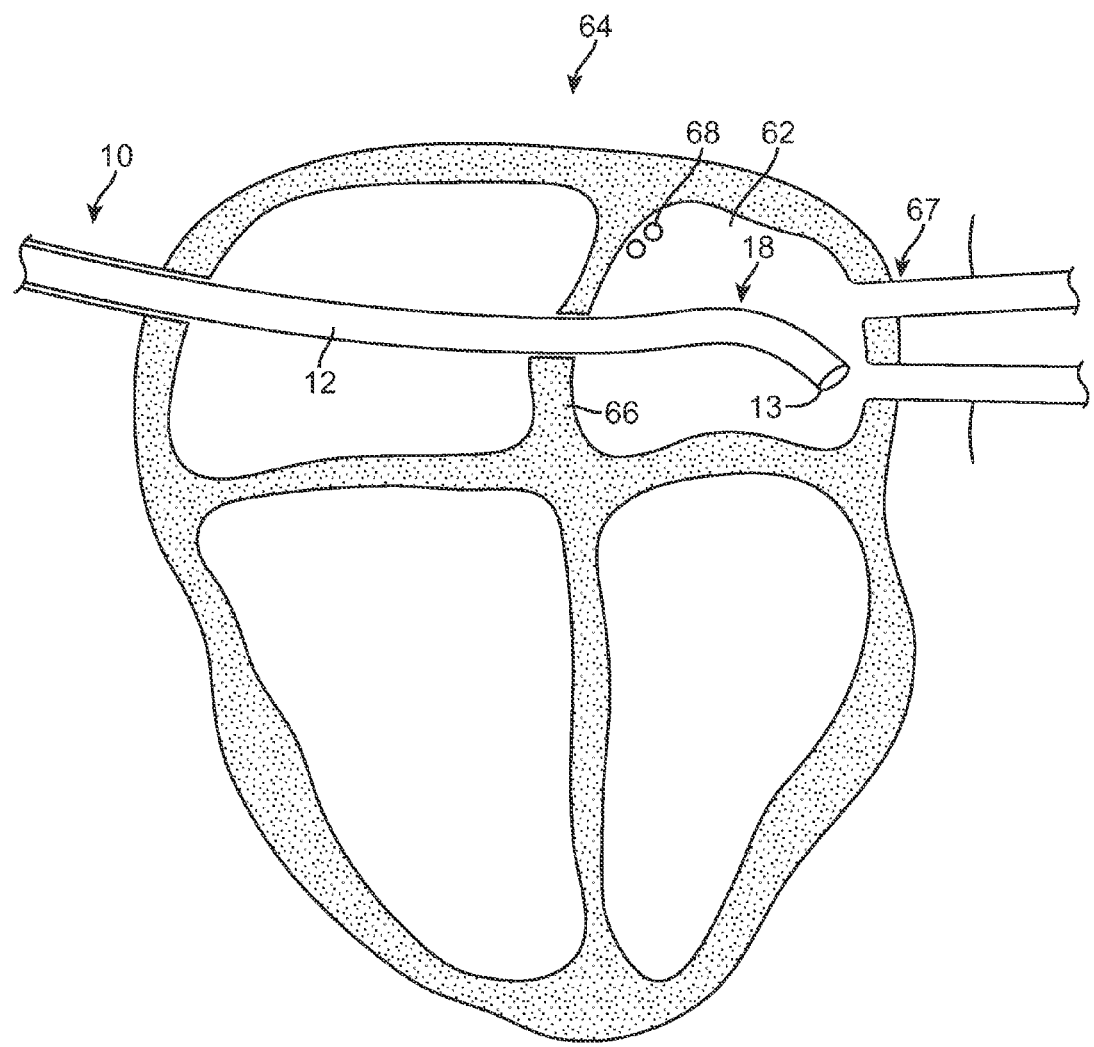
Figure 5C:
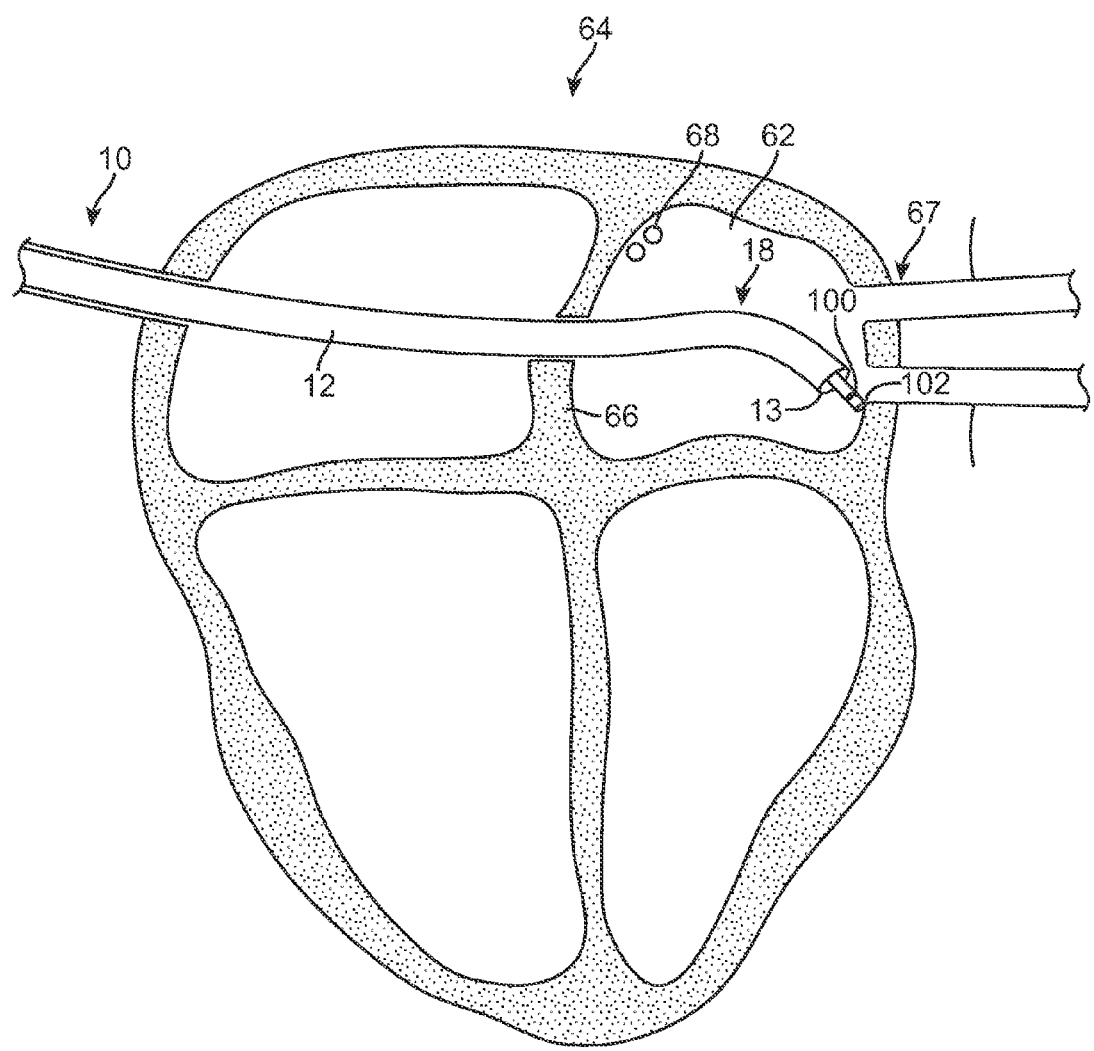

Once the distal end 13 of the elongated body 12 passes through the atrial septum 66, the steering mechanism 17 on the handle 14 (not shown here; see FIGS. 1A and 1B) of the sheath 10 is operated to tension the right steering wire 28a (shown in FIGS. 2A and 2B) to steer the distal end 13 into the first bending configuration 18 to point the distal end 13 towards the left pulmonary veins 67, as shown in FIG. 5B. Once the distal end 13 is properly placed, the catheter 100 is advanced through the lumen 30 in the elongated body 12 until the distal end 102 of the catheter 100 extends distally from the elongated body 12 and contacts a first target tissue site in or around the left pulmonary veins 67, as shown in FIG. 5C. Next, the catheter 100 is operated to map and/or ablate the first target tissue site.

Figure 5D:
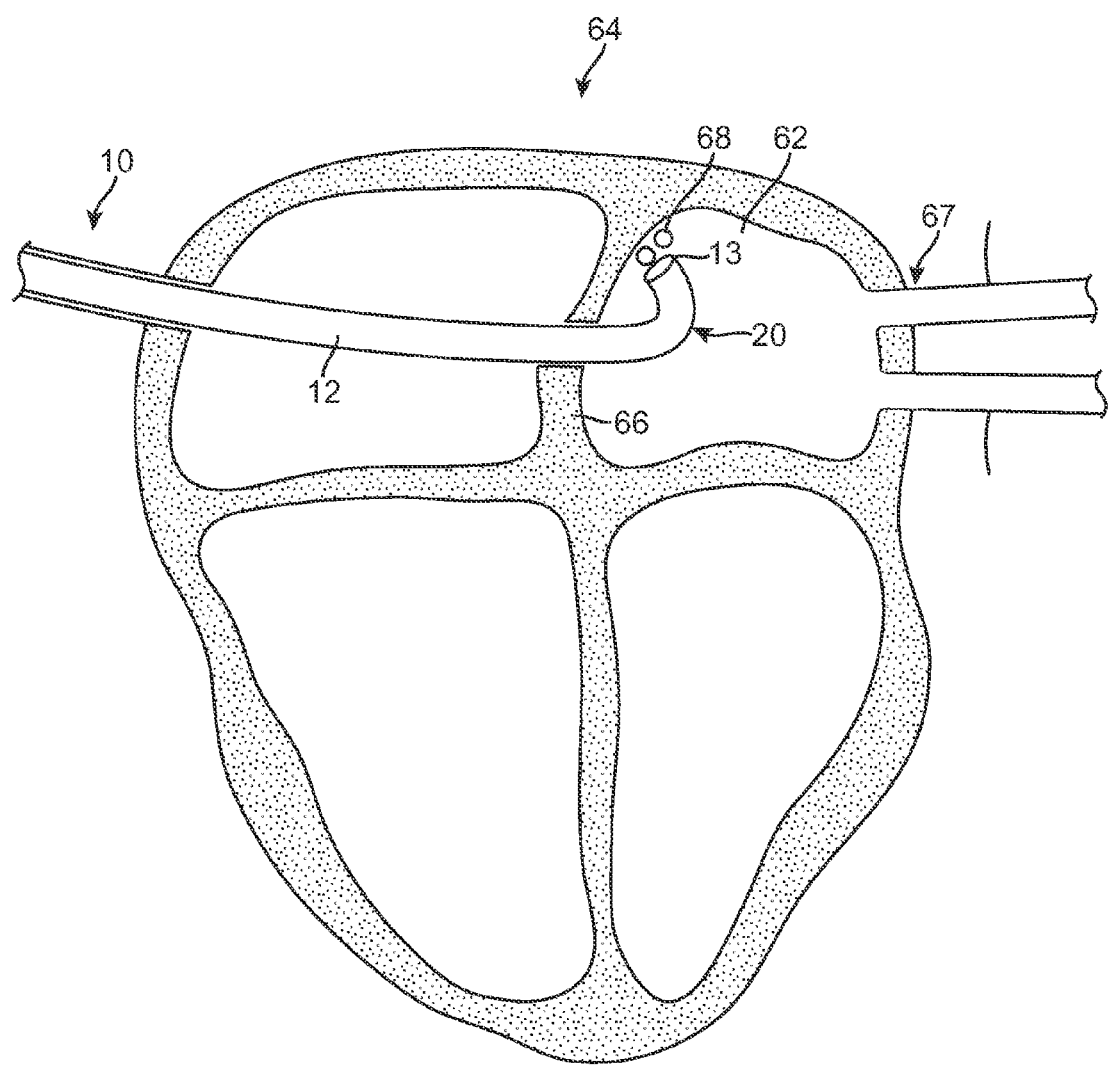
Figure 5E:
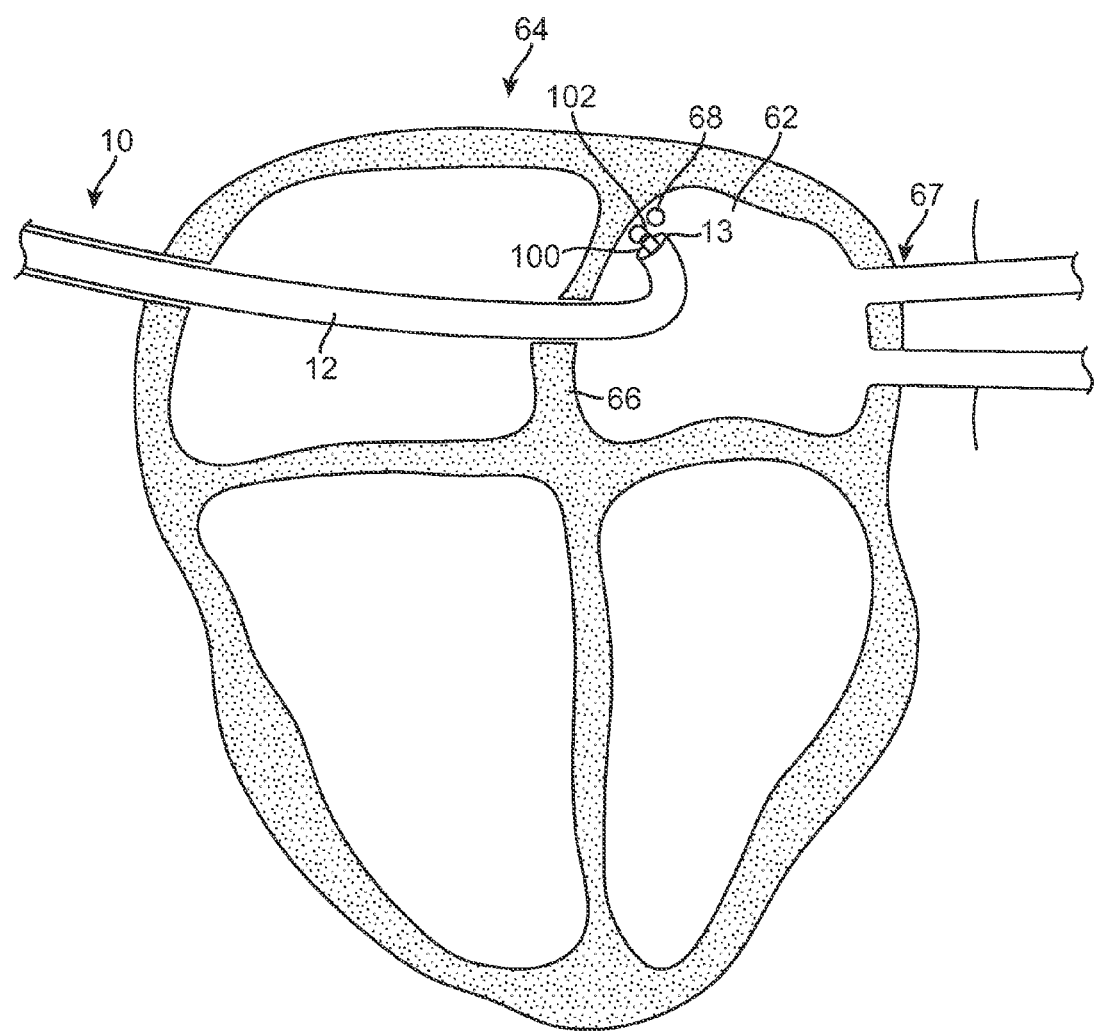

Once the ablation procedure at the first target tissue site is complete, the catheter 100 is proximally retracted into the elongated body 12. Then, the steering mechanism 17 on the handle 14 of the sheath 10 is operated to tension the left steering wire 28b to steer the distal end 13 into the second bending configuration 20 to point the distal end 13 towards the right pulmonary veins 68, as shown in FIG. 5D. Once the distal end 13 is properly placed, the catheter 100 is again advanced through the lumen 30 of the elongated body 12 until the distal end 102 of the catheter 100 extends distally from the elongated body 12 and contacts a second target tissue site in or around the right pulmonary veins 68, as shown in FIG. 5E. The catheter 100 is then operated to map and/or ablate the second target tissue site.

After the mapping/ablation, the catheter 100 is proximally retracted into the elongated body 12 and the catheter 100 and the sheath 10 are removed from the patient. It should be well understood that the above-described ablation procedure could alternatively be performed by first steering the catheter sheath 10 towards the right pulmonary veins 68 and then steering the catheter sheath 10 towards the left pulmonary veins 67. Although the method describes only two mapping and/or ablating procedures, it should be well understood that the method may include more than two mapping and/or ablating procedures. For example, the method may includes multiple mapping and/or ablating procedures while the sheath 10 is in the first bending configuration 18 before steering the sheath 10 into the second bending configuration 20.

Although particular embodiments of the disclosed inventions have been shown and described, it will be understood that it is not intended to limit the disclosed inventions to the preferred embodiments, and it will be obvious to those skilled in the art that various changes and modifications may be made without departing from the scope of the inventions.

For example, although the bending directions of the catheter guide sheath are shown as being 180 degrees apart, it should be understood that the bending directions may be greater than or less than 180 degrees apart. By way of another example, the bending directions may be 90 degrees apart. Further, although the catheter guide sheath is shown as having two bent configurations, it should be understood that the sheath may have more than two bent configurations. By way of yet another example, the catheter guide sheath may have three or four bent configurations that may be symmetrically or asymmetrically disposed around a central axis. Still further, rather than the outer coating 22 with different durometer sections depicted in FIGS. 4A-4F, the coil 42 may be formed of a coated wire where the wire coating has sections with varying stiffness profiles. In other words, the coil 42 may include sections with varying bending properties, while the outer coating has uniform bending properties.

Thus, the disclosed inventions are intended to cover alternatives, modifications, and equivalents, which may be included within the scope of the disclosed inventions, as limited and defined only by the following claims and their equivalents.

What is claimed is:

1. A steerable catheter sheath, comprising:
   an elongated member having a distal end, a proximal end and a lumen extending between the proximal end and the distal end, wherein the lumen is configured for receiving a catheter therein, the elongated member comprising an elongated resilient tube having a first plurality of notches in a first lateral side thereof and a second plurality of notches in a second lateral side thereof, and wherein the respective first and second lateral sides of the tube have different bending properties;
   a first steering wire comprising a distal end coupled to the first lateral side of the elongated member, wherein tensioning the first steering wire bends the distal end of the elongated member in a first direction to create a first bending configuration; and
   a second steering wire comprising a distal end coupled to the second lateral side of the elongated member, wherein tensioning the second steering wire bends the distal end of the elongated member in a second direction to create a second bending configuration,
   wherein a shape of the first bending configuration is different from a shape of the second bending configuration;
   wherein the tube further comprises a plurality of slits in a portion of the first lateral side of the tube for allowing the portion of the tube to bend when the elongated member is steered into the second bending configuration and preventing the portion of the tube from bending when the elongated member is steered into the first bending configuration, and wherein a fulcrum point of the first lateral side of the tube is located between the slits and the notches in the first lateral side of the tube distal to a fulcrum point of the second lateral side of the tube.

2. The steerable catheter sheath of claim 1, further comprising
   a handle coupled to the proximal end of the elongated member; and
   a steering mechanism mounted to the handle, wherein the first and second steering wires have proximal ends coupled to the steering mechanism, such that operation of the steering mechanism tensions one of the first and second steering wires.

3. The steerable catheter sheath of claim 1, wherein the first bending configuration has a first radius of curvature, and the second bending configuration has a second radius of curvature different from the first radius of curvature.

4. The steerable catheter sheath of claim 1, wherein the first plurality of notches are configured for bending the distal end of the elongated member into the first bending configuration and the second plurality of notches are configured for bending the distal end of the elongated member into the second bending configuration.

5. A catheter assembly, comprising:
   the steerable catheter sheath of claim 1; and
   the catheter of claim 1, wherein the catheter is a tissue ablation catheter disposed within the lumen of the elongated member.

6. A method of using the catheter assembly of claim 5, comprising:
   introducing the elongated member from a right atrium through an atrial septum into a left atrium;
   tensioning the first steering wire to bend the elongated member in the first direction into the first bending configuration to point the distal end of the elongated member towards a right pulmonary vein;
   advancing the ablation catheter through the lumen of the elongated member such that the ablation catheter distally extends from the elongated member to contact a first target tissue site within or adjacent to the right pulmonary vein;
   ablating the first target tissue site with the ablation catheter;
   retracting the ablation catheter into the elongated member;
   tensioning the second steering wire to bend the elongated member in the second direction into the second bending configuration to point the distal end of the elongated member towards a left pulmonary vein;
   advancing the ablation catheter through the lumen of the elongated member such that the ablation catheter distally extends from the elongated member to contact a second target tissue site within or adjacent to the left pulmonary vein;
   ablating the second target tissue site with the ablation catheter; and
   retracting the ablation catheter into the elongated member.

7. The method of claim 6, wherein tensioning the first steering wire and tensioning the second steering wire comprise operating a steering mechanism on the proximal end of the elongated member.

8. The method of claim 6, wherein tensioning the first steering wire comprises compressing the first lateral side of the distal end of the elongated member; and
   wherein tensioning the second steering wire comprises compressing the second lateral side of the resilient tube.

9. The method of claim 8, wherein tensioning the first steering wire further comprises compressing the first lateral side of the resilient tube and expanding the second lateral side of the resilient tube; and
   wherein tensioning the second steering wire further comprises compressing the second lateral side of the resilient tube and expanding the first lateral side of the resilient tube.

10. A method for positioning a catheter in a body, comprising:
    providing a steerable guide sheath comprising
      an elongated member having a distal end, a proximal end and a lumen extending between the proximal end and the distal end, wherein the lumen is configured for receiving the catheter therein, the elongated member comprising an elongated resilient tube having a first plurality of notches in a first lateral side thereof and a second plurality of notches in a second lateral side thereof, and wherein the respective first and second lateral sides of the tube have different bending properties;
      a first steering wire comprising a distal end coupled to the first lateral side of the elongated member, wherein tensioning the first steering wire bends the distal end of the elongated member in a first direction to create a first bending configuration; and
      a second steering wire comprising a distal end coupled to the second lateral side of the elongated member, wherein tensioning the second steering wire bends the distal end of the elongated member in a second direction to create a second bending configuration,
      wherein a shape of the first bending configuration is different from a shape of the second bending configuration;
      wherein the tube further comprises a plurality of slits in a portion of the first lateral side of the tube for allowing the portion of the tube to bend when the elongated member is steered into the second bending configuration and preventing the portion of the tube from bending when the elongated member is steered into the first bending configuration, and wherein a fulcrum point of the first lateral side of the tube is located between the slits and the notches in the first lateral side of the tube distal to a fulcrum point of the second lateral side of the tube;

introducing the steerable guide sheath into an anatomical cavity;

introducing the catheter into the guide sheath;

deflecting a distal end of the guide sheath in the first direction into the first bending configuration to point the distal end of the guide sheath towards a first target site;

operating the catheter to perform a medical procedure at the first target site;

deflecting the distal end of the guide sheath in the second direction into the second bending configuration different from the first bending configuration to point the distal end of the guide sheath toward a second target site different from the first target site; and operating the catheter to perform another medical procedure at the second target site.

11. The method of claim 10, further comprising:

advancing the catheter within the guide sheath until a distal end of the catheter extends distally from the distal end of the guide sheath adjacent to the first target site when the distal end of the guide sheath is in the first bending configuration;

retracting the catheter within the guide sheath prior to deflecting the distal end of the guide sheath into the second bending configuration; and advancing the catheter within the guide sheath until the distal end of the catheter extends distally from the distal end of the guide sheath adjacent to the second target site when the distal end of the guide sheath is in the second bending configuration.

12. The method of claim 10, wherein the anatomical cavity is a heart chamber, the first target site is a right pulmonary vein, and the second target site is a left pulmonary vein.

* * * * *